United States Patent
Song et al.

(10) Patent No.: US 12,370,205 B2
(45) Date of Patent: Jul. 29, 2025

(54) COMPOSITION FOR PREVENTING OR TREATING FINE DUST-INDUCED RESPIRATORY DISEASE COMPRISING MIXTURE (RGX-365) COMPRISING GINSENOSIDES RG2, RG4, RG6 AND RH1, AS ACTIVE INGREDIENT, AND PREPARATION METHOD THEREOF

(71) Applicant: AREZ CO., LTD., Daejeon (KR)

(72) Inventors: Gyu Yong Song, Sejong (KR); Jee Hyun Lee, Daejeon (KR); Soo Hyun Cho, Daejeon (KR); Hee Young Won, Daegu (KR); Wonhwa Lee, Suwon-si (KR); Sae-Kwang Ku, Daegu (KR); Ji-Eun Kim, Incheon (KR); Jong-Sup Bae, Daegu (KR)

(73) Assignee: AREZ CO., LTD., Daejeon (KR)

( * ) Notice: Subject to any disclaimer, the term of this patent is extended or adjusted under 35 U.S.C. 154(b) by 722 days.

(21) Appl. No.: 17/602,684

(22) PCT Filed: Apr. 7, 2020

(86) PCT No.: PCT/KR2020/004656
§ 371 (c)(1),
(2) Date: Oct. 8, 2021

(87) PCT Pub. No.: WO2020/209567
PCT Pub. Date: Oct. 15, 2020

(65) Prior Publication Data
US 2022/0160738 A1     May 26, 2022

(51) Int. Cl.
| | |
|---|---|
| A61K 31/704 | (2006.01) |
| A23L 2/52 | (2006.01) |
| A23L 33/105 | (2016.01) |
| A61P 11/00 | (2006.01) |

(52) U.S. Cl.
CPC ............. *A61K 31/704* (2013.01); *A23L 2/52* (2013.01); *A23L 33/105* (2016.08); *A61P 11/00* (2018.01); *A23V 2002/00* (2013.01)

(58) Field of Classification Search
CPC ....... A23L 33/105; A23L 33/125; A61P 11/00
See application file for complete search history.

(56) References Cited

U.S. PATENT DOCUMENTS

2015/0297727 A1* 10/2015 Zhan ................ C07J 17/005
514/26

FOREIGN PATENT DOCUMENTS

| | | |
|---|---|---|
| EP | 2815746 A1 | 12/2014 |
| KR | 10-1363074 B1 | 2/2014 |
| KR | 10-1577111 B1 | 12/2015 |
| KR | 10-1625474 B1 | 5/2016 |
| KR | 10-1783295 B1 | 9/2017 |
| KR | 10-1897811 B1 | 9/2018 |

OTHER PUBLICATIONS

International Search Report issued for International Application No. PCT/KR2020/004656 on Jul. 15, 2020, 4 pages.
Lee, W. et al, Inhibitory effects of protopanaxatriol type ginsenoside fraction (Rgx365) on particulate matter-induced pulmonary injury, Journal of Toxicology and Environmental Health, Part A, Electronic publication on Mar. 27, 2019, vol. 82, No. 5, pp. 338-350, inner pp. 1-13.
Lee, J. H. et al, Ginsenosides from Korean Red Ginseng ameliorate lung inflammatory responses: inhibition of the MAPKs/NF-KB/c-Fos pathways, Journal of Ginseng Research, Electronic publication on Jun. 8, 2017, vol. 42, pp. 476-484.
Song, H. et al., Respiratory Protective Effect of Salvia plebeia R. Br. Extracts against Ambient Particulate Matter-induced Airway Inflammation, Korean J. Medicinal Crop Sci., 25(5), 269-281, 2017.
Kim, Y. S. et al., Differential expression of protein kinase C subtypes during ginsenoside Rh2-Induced apoptosis in SK-N-BE(2) and C6Bu-1 cells, Arch Pharm Res., 23(5), 518-524, 2000.
Shibata, S., Chemistry and cancer preventing activities of ginseng saponins and some related triterpenoid compounds, J Korean Med Sci., 16(suppl), S28-37, 2001.
Tachikawa, E. et al., In vitro inhibition of adrenal catecholamine secretion by steroidal metabolites of ginseng saponins, Biochem Pharmacol., 66(11), 2213-2221, 2003.
Tsai, S. C. et al., Stimulation of the secretion of luteinizing hormone by ginsenoside-Rb1 in male rats, Chin J Physiol., 46(1), 1-7, 2003.
Kim, J. H. et al., Effect of Korean Red Ginseng on Artificial Sand Dust (ASD) Induced Allergic Lung Inflammation, Biomedical Science Letters, 20(3), 173-179, 2014.
Lee, J. H. et al., Anti-wrinkle Effect of Rare Ginsenosides, Produced from Ginsenoside Rd, Kor J Aesthet Cosmetol., 13(6), 909-916, 2015.

* cited by examiner

*Primary Examiner* — Pancham Bakshi
(74) *Attorney, Agent, or Firm* — ROTHWELL, FIGG, ERNST & MANBECK, P.C.

(57) ABSTRACT

The present invention relates to a composition, for preventing or treating a fine dust-induced respiratory disease, comprising a mixture (Rgx 365), comprising ginsenosides Rg2, Rg4, Rg6 and Rh1, as an active ingredient, a preparation method thereof, and a functional health food, for preventing or relieving a fine dust-induced respiratory disease, comprising same. The present invention exhibits excellent effects on permeability reduction, reactive oxygen (ROS) generation reduction, leucocyte reduction and cytokine generation reduction in a model for fine dust-induced inflammatory response, and thus can be utilized for preventing and treating a fine dust-induced respiratory disease.

2 Claims, 5 Drawing Sheets

* Rgx : Example 1

FIG. 7

COMPOSITION FOR PREVENTING OR TREATING FINE DUST-INDUCED RESPIRATORY DISEASE COMPRISING MIXTURE (RGX-365) COMPRISING GINSENOSIDES RG2, RG4, RG6 AND RH1, AS ACTIVE INGREDIENT, AND PREPARATION METHOD THEREOF

CROSS REFERENCE TO RELATED APPLICATION(S)

This application is a 35 U.S.C. 371 National Phase Entry Application from PCT/KR2020/004656, filed on Apr. 7, 2020 and designating the United States, which claims priority based on Korean Patent Application Nos. 10-2019-0041447 filed on Apr. 9, 2019 and 10-2019-0041458 filed on Apr. 9, 2019, all of the disclosures of which are incorporated herein by reference in their entirety.

TECHNICAL FIELD

The present disclosure relates to a composition comprising a mixture (RGX-365) containing ginsenosides Rg2, Rg4, Rg6, and Rh1 as an active ingredient for preventing or treating a fine dust-induced respiratory disease, and a preparation method therefor.

BACKGROUND ART

Recently, as the concentration of fine dust continues to increase, social interest in fine dust and its effects on the human body is increasing. In fine dust, various substances including carbonaceous matter (soot, organic carbons of biological organisms), ionic matter (chlorine, nitric acid, ammonium, sodium, calcium, and the like), metallic matter (arsenic, lead, mercury, and the like), polycyclic aromatic hydrocarbons (benzopyrene and the like), etc. are detected. Increased concentrations of fine dust may give rise to the exacerbation of conjunctivitis, sinusitis, tympanitis, bronchitis, asthma, and chronic obstructive pulmonary disease and the onset of pneumonia, angina pectoris, myocardial infarction, lung cancer, etc. as well as blurring vision and making an uncomfortable sensation. Thus, it has been reported that exposure to fine dust is associated with an increase in mortality as well as the occurrence of respiratory and cardiovascular diseases (Jang, A. S., J Korean Med Fine dust is defined as airborne particulate matter (PM) as small as 10 μm or less in diameter. Particle matter with a diameter of 10 μm or less is called $PM_{10}$. Of $PM_{10}$, relatively large particle matter with a size of 2.5 μm to 10 μm is accounted for by airborne dust mainly from roads or soil while particulate matter with a size of 2.5 μm or less (called ultrafine dust or $PM_{2.5}$) is generated in the process of combusting fossil fuel, like automobile exhaust gas or plant chimney smoke or accounted for by dust secondarily generated through chemical reactions of gas-type air pollutants in air (Kwon, Ho-Chang, Korean Social Trends 2014, 281-287, 2014).

Having very small sizes, fine dust can go through the airway and reach the alveoli to cause inflammation, which leads to the incurrence of symptoms including chest tightness, stridor, cough, etc. A great number of respiratory diseases is associated with airway inflammation. As a rule, inflammation in the airway increases the absolute total number of granulocytes and lymphocytes in bronchoalveolar lavage fluid and makes infiltration into the airway and alveoli. In addition, inflammatory cytokines, such as TNF-α, IL-4, IL-5, IL-6, IL-13, IL-33, etc., secreted from inflammatory cells, such as eosinophils, Th2 cells, mast cells, etc., increases the size of mucous cells and the amount of mucus, inducing an inflammatory response. Of the granulocytes known to be involved in inflammation, eosinophils help Th2 cells produce T cells when the airway responses to an antigen, and Th2 cytokine IL-5 and eotaxin released from mast cells contribute to the production and activation of eosinophils.

Inhalation of fine dust may cause bronchial inflammation which leads to the onset of chronic bronchitis, asthma, allergic alveolitis, etc., when lasting for a long period of time. Chronic obstructive pulmonary disease (COPD), representative of fine dust-induced diseases, is characterized by pulmonary function insufficient and breathing difficulty due to abnormal inflammatory responses. Among fine dust ingredients, particularly diesel exhaust particles (DEPs) increase the secretion of IL-17A to exacerbate bronchial asthma. Fine dust is highly apt to cause or aggravate various diseases including stroke, dementia, arteriosclerosis, hypertension, and circulatory disorder as well as respiratory diseases. In addition, fine dust may allow infection into the respiratory system by inhibiting the inactivation or clearance of bacteria in pulmonary tissues.

Recently, the atmospheric environment has increasingly become abundant in yellow dust, $PM_{10}$, $PM_{2.5}$, and ultrafine dust to which human bodies are more frequently exposed. In addition, industrial nanoparticles that have rapidly expanded the application scope thereof are brought into contact with the human bodies. Such fine dust and harmful chemicals contained in fine dust are known to have noxious influences on the human body through bronchial inflammatory mechanisms such as oxidative stress and inflammatory responses. However, there are no noticeable countermeasures against fine dust-induced bronchitis. Thus, attention has been increasingly paid to natural materials capable of protecting the respiratory organs against the inhalation of fine dust (Song, Hyoung-Woo, et al., Korean J. Medicinal Crop Sci., 25(5), 269-281, 2017).

The term "ginsenoside" is a compound word of ginseng and glycoside. Unlike saponins found in other plants, ginsenosides are known to have unique chemical structures and pharmaceutical efficacy. A ginsenoside is a neutral glycoside in which glucose, arabinose, xylose, rhamnose, or so on is linked to the dammarane skeleton of triterpenoid lineage. As many as about 30 chemical structures have been revealed up to now and are divided by structural characteristics into protopanaxadiol (PPD) family (19 members), protopanaxatriol (PPT) family (10 members), and oleanane family (1 member).

In fresh or white ginseng, the ginsenosides Rg1, Re, Rf, Rh1, Rb1, Rb2, Rc, and Rd are predominant, amounting to 80-90% of the total ginsenosides. Rare ginsenosides are formed as the predominant ginsenosides take parts of sugars off or undergo dehydration. A trace amount of rare ginsenosides is detected in water or alcohol extracts of ginseng. Rare ginsenosides spun off from predominant ginsenosides are responsible for pharmacological activities of ginsenosides and are known to have main efficacies including immunopotentiation, anti-inflammatory, anti-allergic, anti-cancer, anti-hypertensive, anti-cholesterol, anti-thrombotic, anti-aging, and anti-oxidative activities, brain activity promotion, and skin care effects (Kim, Y. S. et al., Arch Pharm Res., 23(5), 518-524, 2000; Shibata, S., J Korean Med Sci., 16(suppl), S28-37, 2001; Tachikawa, E. et al., Biochem Pharmacol., 66(11), 2213-2221, 2003; Tsai, S. C. et al., Chin J Physiol., 46(1), 1-7, 2003).

Rg2, which is one of rare ginsenosides, improves memory, suppresses catecholamine secretion, and activates plasmin to inhibit the aggregation of platelets while Rh1 has anticancer activity of inhibiting the metastasis of cancer cells and exhibits a hepaprotective action. Rh4 and Rh6 were reported to exhibit wrinkle reduction and a skin whitening effect, but their efficacies still remain unknown. For pharmacological effects of rare ginsenosides on respiratory diseases, reference may be made to documents [Lee, J. H. et al., J Ginseng Res., 42, 476-484, 2018], which discloses inhibitory effects of the ginsenoside Rg2 or ginseng extract on pulmonary inflammation, and [Kim, J. H. et al., Biomedical Science Letters, 20(3), 173-179, 2014], which discloses an inhibitory effect of red ginseng on artificial sand dust (ASD)-induced allergic lung inflammation. However, nowhere are concrete therapeutic effects of a ginsenoside mixture on fine dust-induced respiratory disease disclosed in the documents reported previously.

Preparation methods for a mixture containing ginsenosides are disclosed in Korean Patent Number 10-1897811, which teaches that a mixture of ginsenosides Rh1, Rg4, and Rg6 is produced on a mass scale from ginsenoside Re by adding distilled water to ginsenoside Re and steaming the same, and Korean Patent Number 10-1625474 which teaches a mass production method for ginsenoside Rh4 in which ginsenoside Re is added with an organic acid and steamed.

However, mass production of rare ginsenosides with excellent physiological activity, including Rg2, has not been actively studied, and thus there is a need for research thereon.

DISCLOSURE OF INVENTION

Technical Problem

An aspect of the present disclosure is to provide a composition comprising as an active ingredient for preventing or treating fine dust-induced respiratory disease a mixture (RGX-365) containing ginsenosides Rg2, Rg4, Rg6, and Rh1.

Another aspect of the present disclosure is to provide a method for preparing ginsenoside Rg2-enriched mixture (RGX-365) containing ginsenosides Rg2, Rg4, Rg6, and Rh1 from ginsenoside Re, and a mixture (RGX-365) containing ginsenosides Rg2, Rg4, Rg6, and Rh1, prepared thereby.

Solution to Problem

The present disclosure provides a composition comprising as an active ingredient for preventing or treating a fine dust-induced respiratory disease a mixture (RGX-365) containing ginsenosides Rg2, Rg4, Rg6, and Rh1.

The mixture (RGX-365) containing ginsenosides Rg2, Rg4, Rg6, and Rh1 may further contain a pharmaceutically acceptable salt and may be prepared using any method that is typically used in the art, without limitations, and preferably using the following method.

The present disclosure provides a method for preparing a mixture containing ginsenosides Rg2, Rg4, Rg6, and Rh1, the method comprising the steps of:

(first process) mixing 100 parts by weight of ginsenoside Re with 130-160 parts by weight of distilled water;

(second process) reacting the mixture of the first process for 4-6 hours at a temperature of 110-140° C. under a pressure condition of 0.11-0.16 MPa; and

(third process) subjecting the reaction mixture of the second process to column separation to afford a mixture containing ginsenosides Rg2, Rg4, Rg6, and Rh1.

The ginsenoside Re is converted into ginsenosides Rg2, Rg4, Rg6, and Rh1 through the following Reaction Scheme 1:

[Reaction Scheme 1]

-continued

Rg1 = C$_{42}$H$_{72}$O$_{14}$
Mw: 800.49

Rh1(R,S) = C$_{36}$H$_{62}$O$_9$
Mw: 638.44

The first process and the second process are steps of mixing ginsenoside Re with distilled water and reacting the same at a high temperature under a high pressure. In a more particular embodiment, ginsenoside Re is mixed with 140-150 parts by weight of distilled water and subjected to a reaction for 4-6 hours at a temperature of 110-140° C. under a pressure of 0.11-0.16 MPa, followed by column separation to afford a mixture of ginsenosides Rg2, Rg4, Rg6, and Rh1 with ginsenoside Rg2 amounting to 35% by weight or greater therein.

The mixture of ginsenosides Rg2, Rg4, Rg6, and Rh1, prepared through the processes, contains 35-45% by weight of ginsenoside Rg2, 30-40% by weight of ginsenoside Rg4, 10-20% by weight of ginsenoside Rg6, and 1-5% by weight of ginsenoside Rh1.

However, when ginsenoside Re is added with water or reacted at a high temperature under a high pressure beyond the condition, undesired results are obtained, e.g., ginsenoside Re is not sufficiently converted and remains in a significant amount, or the mixture may not contain all of the ginsenosides Rg2, Rg4, Rg6, and Rh1, but some of the ginsenosides, with ginsenoside Rg2 contained at a content of less than 35% by weight.

Such as, a mixture containing 35-45% by weight of ginsenoside Rg2, 30-40% by weight of ginsenoside Rg4, 10-20% by weight of ginsenoside Rg6, and 1-5% by weight of ginsenoside Rh1 will be referred to as RGX-365, below.

Ginsenoside Re is preferably prepared by separation from a ginseng extract. The ginseng extract may be obtained from any part of ginseng origin, such as roots, fruits, leaves, stems, and so on, and a large amount of ginsenoside Re may be prepared particularly from ginseng leaves. The ginseng used for extracting ginsenoside Re is a perennial plant belonging to the genus Panax and may be at least one selected from Korean ginseng (Panax ginseng), American ginseng (Panax quinquefolia), South China ginseng (Panax notoginseng), Japanese ginseng (Panax japonicus), Himalayan ginseng (Panaxa pseudoginseng), Vietnamese ginseng (Panax vietnamensis), Panax elegatior, Panax wangianus, Panax bipinratifidus, and Panax angustifolium, with the most preference for Korean ginseng (Panax ginseng) because of the highest content of saponins therein, but is not limited thereto.

The ginseng extract may be obtained by extraction from ginseng with water, a C1 to C4 alcohol, or a combination thereof serving as a solvent. The C1 to C4 alcohol may be selected from the group consisting of methanol, ethanol, propanol, iso-propanol, butanol, and iso-butanol. The solvent for preparing the ginseng extract, that is, water, a C1 to C4 alcohol, or a combination thereof, may be used in a 1- to 40-fold larger volume than the weight of ginseng (1-40 liters per kg of ginseng) and particularly in a 1- to 20-fold larger volume, and the process may be repeated one to four times.

For use in the column separation, a synthetic adsorbent may be Trilite GSH-20, GSP-07, GSP-25, GSP-50, Diaion HP-10, HP-20, HP-21, HP-30, HP-40, HP-50, SP800, SP825, SP850, SP875, SP205-207, HP1MG, HP2MG, etc., with preference for GSH-20, HP-20, and SP825.

Another aspect of the present disclosure is concerned with a mixture containing ginsenosides Rg2, Rg4, Rg6, and Rh1, prepared through the first to the third process. Exhibiting excellent therapeutic effects on fine dust-induced respiratory diseases, the mixture can be available for a pharmaceutical composition for preventing or treating fine dust-induced respiratory diseases or a health functional food for preventing or alleviating fine dust-induced respiratory diseases.

The respiratory disease refers to a disease resulting from chronic inflammation in the airway, the bronchus, and the lung, with the attendant generation of cough, phlegm, breathing difficulty, and fever. Particularly, the respiratory disease may be selected from the group consisting of inflammatory lung disease, asthma, chronic obstructive pulmonary disease, allergic rhinitis, cough, bronchitis, laryngopharyngitis, tympanitis, tonsillitis, sinusitis, pneumonia, pulmonary fibrosis, and laryngitis, but is not limited thereto.

The pharmaceutical composition may be formulated, together with a pharmaceutically acceptable carrier, into suitable forms. As used herein, the term "pharmaceutically acceptable" in context with a pharmaceutical composition means pertaining to physiologically allowable or generally not causative of an allergic response such as gastrointestinal disorder, dizziness, etc., or a similar response after administration to humans. In addition, the composition may be formulated into oral dosage forms such as pulvises, granules, tablets, capsules, suspensions, emulsions, syrups, aerosols, etc., or into parenteral dosage forms such as topical agents, suppositories, and sterile injectable solutions according to respective typical methods.

Examples of the carrier, excipient, and diluent available in the composition include lactose, dextrose, sucrose, sorbitol, mannitol, xylitol, erythritol, maltitol, starch, gum arabic, alginate, gelatin, calcium phosphate, calcium silicate, cellulose, methyl cellulose, microcrystalline cellulose, polyvinyl pyrrolidone, water, methyl parahydroxybenzoate, propyl parahydroxybenzoate, talc, magnesium stearate and mineral oil, but are not limited thereto. For formulation, the composition may employ a typical diluent or excipient, such as a filler, a stabilizer, a binder, a disintegrant, a surfactant, etc.

A solid formulation for oral administration may be in the form of a tablet, a pill, a pulvis, a granule, a capsule, etc. Such solid dosage form may be formulated by mixing the ginsenoside mixture of the present disclosure with at least one excipient, such as starch, microcrystalline cellulose, sucrose or lactose, low-substituted hydroxypropyl cellulose, Hypromellose, etc. Also, lubricants such as magnesium stearate and talc may be used in addition to simple excipients. Liquid formulation agents for oral administration can be exemplified by suspensions, solutions for internal use, emulsions, and syrups and may contain various diluents such as humectants, sweeteners, fragrances, and preservatives in addition to commonly used simple excipients such as water, liquid paraffin, etc. Formulations for parenteral administration can be illustrated as sterile aqueous solutions, nonaqueous solvents, suspensions, emulsions, lyophilizates, and suppositories. For nonaqueous solvents and suspensions, propylene glycol, polyethylene glycol, vegetable oil such as olive oil, and injectable esters such as ethyl oleate may be used. As a base for suppositories, Witepsol, Macrogol, Tween 61, cacao butter, laurin, glycerol, gelatin, and the like may be used. For parenteral dosage formulations, the ginsenoside mixture or a pharmaceutically acceptable salt thereof may be sterilized and/or mixed with a preservative, a stabilizer, a hydrator, an emulsion promoter, a salt for osmotic pressure regulation, and/or an auxiliary agent such as a buffer, or other therapeutically useful substances in water to give a solution or a suspension which may be then prepared into an ampoule or vial unit dosage form.

The pharmaceutical composition in the present disclosure may be administered to mammals such as rats, mice, cattle, and human through various routes. All manners of administration may be contemplated: for example, administration may be carried out via oral, intrarectal, intravenous, intramuscular, subcutaneous, and endometrial or intracerebroventricular routes. The administration dose may vary depending on various factors including the age, sex, or body weight of a subject to be treated, the particular disease or pathological condition to be treated, the severity of disease or pathological condition, the time of administration, the route of administration, the absorption, distribution, and excretion rate of a drug, the kind of another drug used, and the determination of a prescriber. The determination of the dose on the basis of these factors is within the level of a person skilled in the art, and the usual dose is in a range of 0.01-2000 mg/kg/day and more preferably in a range of 1-500 mg/kg/day. The dose may be administered once a day or divided into multiple doses. The dose is not intended to limit the scope of the present disclosure in any way.

In another aspect, the present disclosure provides a health functional food comprising a mixture containing ginsenosides Rg2, Rg4, Rg6, and Rh1 as an active ingredient for preventing or alleviating a fine dust-induced respiratory disease.

As used herein, the term "health functional food" refers to a food prepared or processed with a material or ingredient having useful functionality and is intended to encompass, for example, a health supplemental food, a functional food, a nutritional agent, a supplementary, and so on.

The ginsenoside mixture may be added particularly in an amount of 0.001% by weight to 50% by weight, more particularly in an amount of 0.001% by weight to 30% by weight, and most particularly in an amount of 0.001% by weight to 10% by weight, based on the total weight of the health functional food.

The health function food of the present disclosure may be in the form of a tablet, a capsule, a pill, or a solution. The ginsenoside mixture of the present disclosure can be added to various foods, for example, beverages, gum, teas, vitamin complexes, and so on.

Advantageous Effects of Invention

The present disclosure relates to a composition comprising a mixture containing ginsenosides Rg2, Rg4, Rg6, and Rh1 as an active ingredient for preventing or treating a fine dust-induced respiratory disease and a preparation method therefor. According to the present disclosure, a large amount of a ginsenoside Rg2-enriched mixture containing ginsenosides Rg2, Rg4, Rg6, and Rh1 can be easily obtained from ginsenoside Re, and the ginsenoside mixture exhibits a particularly selective therapeutic effect on fine dust-induced respiratory diseases and, as such, can be advantageously used for preventing or treating fine dust-induced respiratory diseases, compared to individual ginsenosides Rg4, Rg6, and Rh1, a ginseng extract, or a red ginseng extract.

BEST MODE FOR CARRYING OUT THE INVENTION

Hereinafter, preferred embodiments of the present disclosure will be described in detail. However, the present disclosure is not limited to the embodiments described herein, but may be embodied in other forms. Rather, the embodiments is provided so that the content presented here is thorough and complete and the spirit of the present disclosure is fully understood to a person skilled in the art.

Example 1

Preparation of Mixture (RGX-365) Containing Ginsenosides Rg2, Rg4, Rg6, and Rh1

To 30.4 g of ginsenoside Re was added 45 ml of distilled water, followed by autoclaving at 121° C. under 0.13 MPa for 6 hours and then column separation.

A synthetic adsorbent was loaded in an amount of 300 g, which was 10-fold larger than that of the material, onto the column and washed with a sufficient amount of an eluent. After 5 liters of distilled water were let to flow through a column, followed by 5 liters of fermented alcohol. Again, 5 liters of water were let to flow through the column, with a care taken to prevent incorporation of bubbles into the column.

The reaction mixture obtained by autoclaving ginsenoside Re for 6 hours was dissolved in a fermented alcohol (50 ml) and distilled water (300 ml). The water fraction was poured to the column. Then, about 5 liters of distilled water were let to flow through the column, followed by a series of 20%, 25%, and 30% fermented alcohols in that order to remove foreign matter. When 35-70% fermented alcohols were applied, an RGX 365 fraction was obtained, and concentrated in a vacuum to give 18 g of the mixture (RGX-365) of Example 1.

Mixtures of Examples 2 and 3 were each obtained in an amount of 18 g in the same manner as in Example 1, with the exception that 48 ml or 40 ml of distilled water was added to 30.4 g of ginsenoside Re, followed by autoclaving at 121° C. under 0.13 MPa for 6 hours and then column separation, as indicated in Table 1, below.

Figure 1:
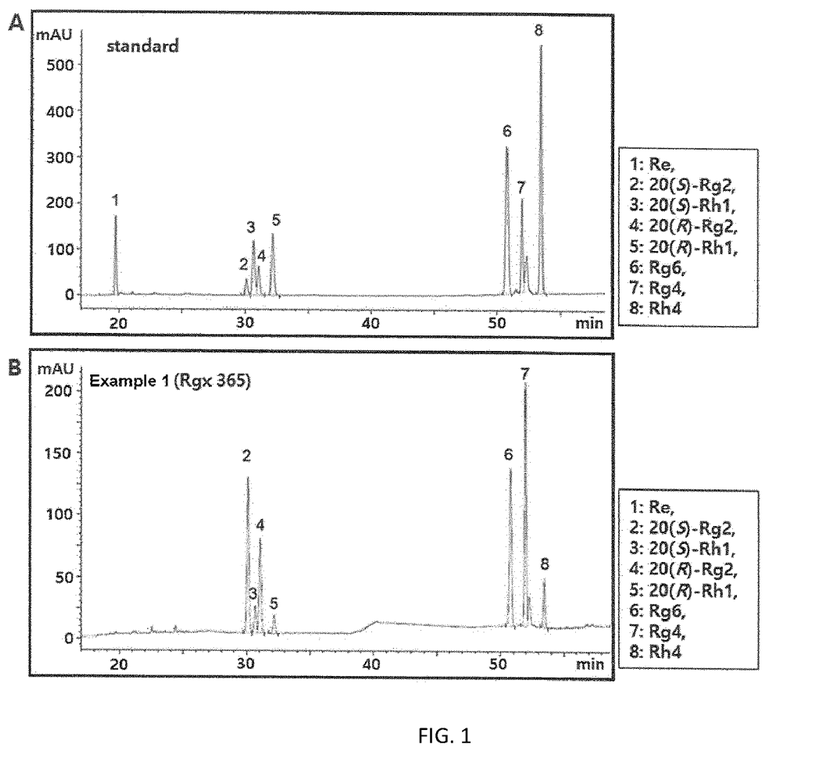
FIG. 1A is a chromatogram obtained by HPLC for reference standard ginsenosides Re, Rg2, Rg4, Rg6, and Rh1, and Rh4.
FIG. 1B is an HPLC chromatogram for ginsenosides contained in the mixture (RGX-365) of Example 1.

Among the mixtures of Examples 1 to 3 obtained above, the mixture of Example 1 was quantitatively analyzed for ginsenosides Rg2, Rg4, Rg6, and Rh1 by HPLC under the conditions of Table 2, below, and the contents thereof are depicted in FIG. 1 and summarized in Table 3.

TABLE 1

| | Mixing condition | |
|---|---|---|
| | Ginsenoside Re (g) | Distilled water (ml) |
| Example 1 | 30.4 | 45 |
| Example 2 | 30.4 | 48 |
| Example 3 | 30.4 | 40 |

TABLE 2

| HPLC Condition | |
|---|---|
| Column | ACE 5-C18 (250 × 4.6 mm) |
| Flow rate | 1.0 ml/min |
| Sample injected | 10 μl |
| Detector | UV 205 nm, Agilent Technologies 1260 infinity |
| Temp. | 40° C. |
| Solvent | A; water, B; acetonitrile |
| | 0-3 min (A from 20% to 40%), |
| | 3-15 min (B from 20% to 23%), |
| | 15-20 min (B from 23% to 33%), |
| | 20-45 min (B from 33% to 40%), |
| | 45-60 min (B from 40% to 68%), |

TABLE 2-continued

| HPLC Condition |
|---|
| 60-65 min (B from 68% to 85%), |
| 65-70 min (B 85%), |
| 70-73 min (B from 80% to 20%), |
| 73-75 min (B 20%) |

TABLE 3

| | Ginsenoside content | |
|---|---|---|
| | g | % |
| Ginsenoside Rg2 | 7.4 | 41.1 |
| Ginsenoside Rg4 | 6.4 | 35.4 |
| Ginsenoside Rg6 | 2.6 | 14.2 |
| Ginsenoside Rh1 | 0.8 | 4.4 |

COMPARATIVE EXAMPLE 1

Preparation of Mixture Containing Ginsenosides Rh1, Rg4, and Rg6

A mixture of Comparative Example 1 was prepared with reference to Example 1 of Korean Patent Number 10-1897811.

First, a mixture of 10 mg of ginsenoside Re and 25 μl of distilled water was treated at 120° C. under 0.13-0.15 MPa for 8 hours in an autoclave. Next, the reaction mixture was concentrated in a rotary evaporator, and the concentrated powder thus obtained was separated and purified to afford a mixture containing ginsenosides Rh1, Rg4, and Rg6 of Comparative Example 1.

COMPARATIVE EXAMPLE 2

Preparation of Comparative Mixture Containing Ginsenosides Rg2, Rg4, Rg6, and Rh1

The same procedure as in Example 1 was carried out, with the exception that 60 ml, instead of 45 ml, of distilled water was added to 30.4 g of ginsenoside Re and then autoclaved at 121° C. under 0.13 MPa for 6 hours, followed by column separation.

COMPARATIVE EXAMPLE 3

Preparation of Comparative Mixture Containing Ginsenosides Rg2, Rg4, Rg6, and Rh1

The same procedure as in Example 1 was carried out, with the exception that 53 ml, instead of 45 ml, of distilled water was added to 30.4 g of ginsenoside Re and then autoclaved at 121° C. under 0.13 MPa for 6 hours, followed by column separation.

COMPARATIVE EXAMPLE 4

Preparation of Comparative Mixture Containing Ginsenosides Rg2, Rg4, Rg6, and Rh1

The same procedure as in Example 1 was carried out, with the exception that 35 ml, instead of 45 ml, of distilled water was added to 30.4 g of ginsenoside Re and then autoclaved at 121° C. under 0.13 MPa for 6 hours, followed by column separation.

COMPARATIVE EXAMPLE 5

Preparation of Comparative Mixture Containing Ginsenosides Rg2, Rg4, Rg6, and Rh1

The same procedure as in Example 1 was carried out, with the exception that 30 ml, instead of 45 ml, of distilled water was added to 30.4 g of ginsenoside Re and then autoclaved at 121° C. under 0.13 MPa for 6 hours, followed by column separation.

Experimental Example 1

Comparison of Ginsenoside Rg2 Content

Among the ginsenosides contained in the mixtures of Examples 1 to 3 and Comparative Examples 1 to 5, ginsenoside Rg2 was quantitatively analyzed by HPLC under the conditions of Table 2 and the contents thereof are summarized in Table 4, below.

TABLE 4

| | Condition | Ginsenoside Rg2 Content (wt %) |
|---|---|---|
| Ex. 1 | Ginsenoside Re 100 wt. part, Distilled water 148 wt. part | 41.1 |
| Ex. 2 | Ginsenoside Re 100 wt. part, Distilled water 158 wt. part | 42.5 |
| Ex. 3 | Ginsenoside Re 100 wt. part, Distilled water 132 wt. part | 37.5 |
| C. Ex. 1 | Ginsenoside Re 100 wt. part, Distilled water 250 wt. part | <10 |
| C. Ex. 2 | Ginsenoside Re 100 wt. part, Distilled water 197 wt. part | 11.5 |
| C. Ex. 3 | Ginsenoside Re 100 wt. part, Distilled water 174 wt. part | <25 |
| C. Ex. 4 | Ginsenoside Re 100 wt. part, Distilled water 115 wt. part | 19.8 |
| C. Ex. 5 | Ginsenoside Re 100 wt. part, Distilled water 100 wt. part | <10 |

As seen in Table 4, when a mixture of 100 parts by weight of ginsenoside Re and 130-160 parts by weight of distilled water was steamed according to the present disclosure, the mixture of ginsenosides Rg2, Rg4, Rg6, and Rh1 thus obtained was measured to contain ginsenoside Rg2 in an amount of 35% by weight or greater.

In contrast to the present disclosure, the content of ginsenoside Rg2 in the final ginsenoside mixture was measured to be 25% by weight or less when distilled water was added in an amount of less than 130 parts by weight or greater than 160 parts by weight to 100 parts by weight of ginsenosides Re. That is, when less than 130 parts by weight of distilled water is added to 100 parts by weight of ginsenoside Re, ginsenoside Re is not sufficiently converted, but remains significantly unreacted, with the consequent low production of ginsenoside Rg2. Given greater than 160 parts by weight of distilled water, ginsenoside Rg2 does not stay in the final mixture, but is further converted to ginsenosides Rg4 and Rg6. Thus, the final mixture increased in the content of ginsenosides Rg4 and Rg6.

Therefore, a method comprising mixing 100 parts by weight of ginsenoside Re with 130-160 parts by weight of distilled water and steaming the mixture according to the present disclosure can enrich ginsenoside Rg2, which is particularly effective for therapy of fine dust-induced respiratory diseases, and as such, is found to be a advantageous preparation method for a pharmaceutical composition for prevention or treatment of find dust-induced respiratory diseases.

Experimental Example 2

Cell Culturing

Mouse lung microvascular endothelial cells (MLMVECs) were obtained as previously reported [Kovacs-Kasa, A. et al., Sci Pages Pulmonol., 1(1), 7-18, 2017].

First, 7-week-old male Balb/c mice (weighing 27 g, Orient Bio Co., Sungnam, Republic of Korea) were acclimated at a temperature of 20-25° C. and a relative humidity of 40-45% for 12 days on ah 12-hr light/12-hr dark cycle. The mice used in experiments were treated according to the guideline for the Care and use of Laboratory Animals at Kyungpook National University (IRB No. KNU 2017-101).

Lung tissues thus obtained were homogenized and then digested at 37° C. for 45-60 min with collagenase A (1 mg/ml). Epithelial cells were purified using anti-PECAM-1 monoclonal antibody magnetic beads (BD Pharmingen, San Diego, Calif.) and grown for 2 days in a growth medium.

For a monolayer culture, the cells were incubated in an endothelial cell basal medium supplemented with EGM-2 MV Bulletkit™ (Lonza, Md.) on a fibronectin-coated culture dish at 37° C. under the atmosphere of 5% $CO_2$ and 95% air.

Experimental Example 3

Cytotoxicity Assay

The mixture of Example 1 according to the present disclosure was examined for cytotoxicity in mouse lung microvascular endothelial cells by MTT (3-(4,5-dimethylthiazol-2-yl)-2,5-diphenyltetrazoliumbromide) assay.

The mouse lung microvascular endothelial cells prepared in Experimental Example 2 were seeded at a density of $5\times10^3$ cells/well into 96-well plates and then incubated for 24 hours with 0, 10, 25, or 50 mg/kg of the ginsenoside mixture (RGX-365) obtained in Example 1. Thereafter, the cells in each well were washed and treated for 4 hours with 100 μl of 1 mg/ml MTT solution. The formazan salt thus formed within the cells was dissolved by adding 150 μl of DMSO, followed by reading absorbance at 540 nm on a microplate reader (Tecan Austria GmbH, Austria). Cell viability was calculated from the absorbance measurements and is depicted in FIG. 2.

Figure 2:
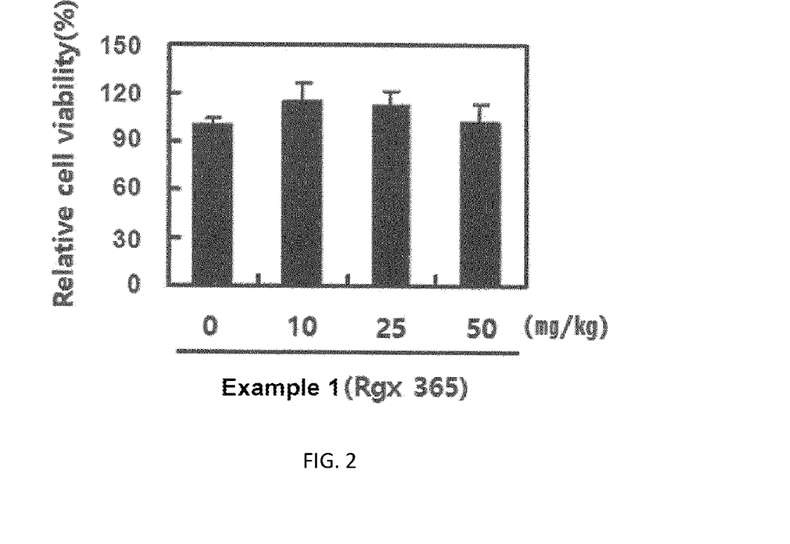
FIG. 2 is a graph showing cell viability of mouse lung microvascular endothelial cells according to treatment concentrations of the mixture (RGX-365) of Example 1 of the present disclosure.

Referring to FIG. 2, the mixture (Rgx 365) of Example 1 according to the present disclosure allowed the cell viability equivalent to that of the non-treated group irrespective of the concentrations used, and thus was demonstrated to have no cytotoxicity.

Experimental Example 4

Inhibitory Effect on Inflammation in Mouse Lung Microvascular Endothelial Cells

Exposure of the human body to fine dust causes acute inflammation, giving rise to various activities including the secretion of cytokines and chemokines, the increase of leukocytes, the generation of reactive oxygen species in the lung, the endotoxin-induced responses of cells and tissues, and so on. These activities lead to the onset or exacerbation of diseases, such as asthma, chronic bronchitis, and airway obstruction. In this context, the mixture of Example 1 according to the present disclosure was examined for inhibitory activity against inflammation through the permeability assay and the measurement of generation change of reactive oxygen species in mouse lung microvascular endothelial cells.

Experimental Example 4-1

Permeability Assay

Permeability to endothelial cells of the mixture of Example 1 of the present disclosure was quantitated according to concentrations by spectrophotometric measurement of the flux of Evans blue-bound albumin across functional cell monolayers using a 2-compartment chamber model as previously described [Bae, J. S. et al., Blood, 118(14), 3952-3959, 2011; Jung, B. et al., BMB Rep., 49(4), 214-219, 2016].

For a permeability assay in the mouse lung microvascular endothelial cells, the cells of Experimental Example 2 were plated at a density of $5 \times 10^4$ cells/well in a Transwell (pore size, 3 µm; diameter, 12 mm) and incubated for 3 days. When reaching confluency of monolayers in the Transwell, the cells were first treated with predetermined concentrations (1, 10, 20, 50, 100, and 200 µg/ml) of the mixture (RGX-365) of Example 1 and then with fine dust ($PM_{2.5}$, 1 mg/ml) for 6 hours. For comparison, reference standard ginsenosides Re, Rg4, Rg6, Rh1, and Rg2, and the ginsenoside mixture of Comparative Example 1 were each applied at a concentration of 200 µg/ml in the same manner as described above. Subsequently, permeability was measured using an ELISA plate reader, and the measurements are depicted in FIGS. 3A and 3B.

Figure 3:
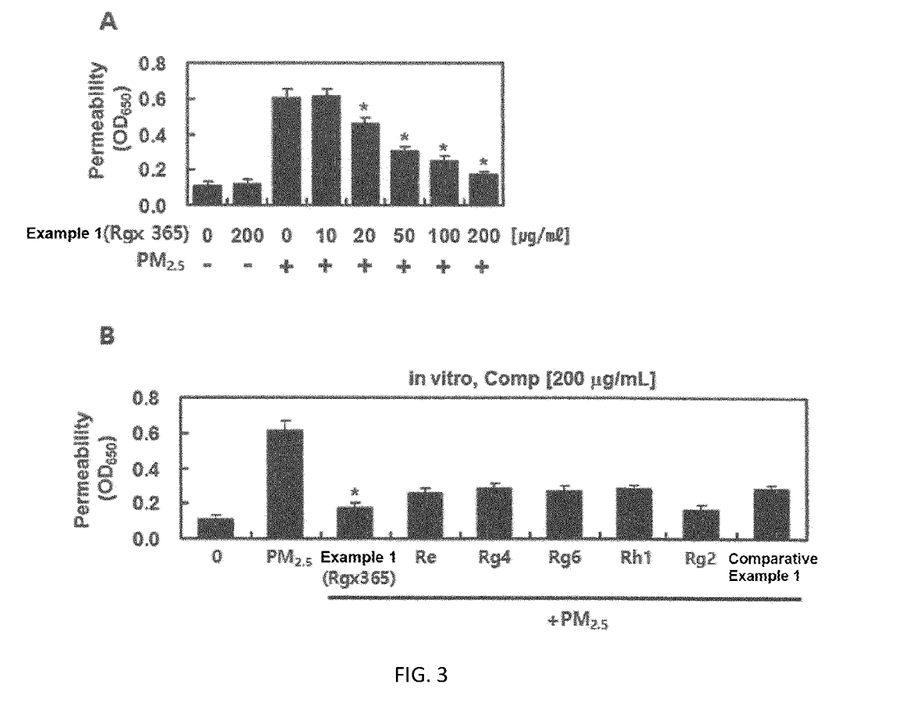
FIG. 3A is a graph showing permeability of fine dust-treated mouse lung microvascular endothelial cells according to treatment concentrations of the mixture (RGX-365) of Example 1 of the present disclosure and FIG. 3B is a graph showing permeability of fine dust-treated mouse lung microvascular endothelial cells according to treatment with the mixture (RGX-365) of Example 1 of the present disclosure, individual ginsenosides Re, Rg4, Rg6, Rh1, and Rg2, and the mixture of Comparative Example 1.

As can be seen in FIGS. 3A and 3B, when applied to mouse lung microvascular endothelial cells having inflammation induced therein by fine dust, the mixture (Rgx 365) of Example 1 according to the present disclosure exhibited a more reductive effect on vascular permeability than the individual ginsenosides Re, Rg4, Rg6, and Rh1 and the ginsenoside mixture of Comparative Example 1.

Therefore, the mixture of ginsenosides Rg2, Rg4, Rg6, and Rh1, prepared by the method of the present disclosure, is particularly selective for the therapy of fine dust-induced respiratory diseases, so that the method is advantageous for preparing a composition for preventing or treating fine dust-induced respiratory diseases.

Experimental Example 4-2

Reactive Oxygen Species (ROS)

Reactive oxygen species (ROS) in the mouse lung microvascular endothelial cells was quantitated by fluorescence microscopy as previously reported [Piao, M. J. et al., Arch Toxicol., 92(6), 2077-2091, 2018]. Primary mouse lung microvascular endothelial cells grown in 4-well glass chamber slides (>90% confluent) were treated with predetermined concentrations (0, 1, 4, 7.5, and 15 mg/kg) of the ginsenoside mixture (RGX-365) of Example 1 and then with fine dust ($PM_{2.5}$, 1 mg/ml), followed by adding DCFDA (2',7'-dichlorofluorescein diacetate, Molecular Probes, Eugene, OR, USA, 10 µM). After 30 min, the medium containing DCFDA was aspirated and the cells were washed. Stained cells were detected by fluorescence microscopy, and the results are given in FIGS. 4A and 4B.

Figure 4:
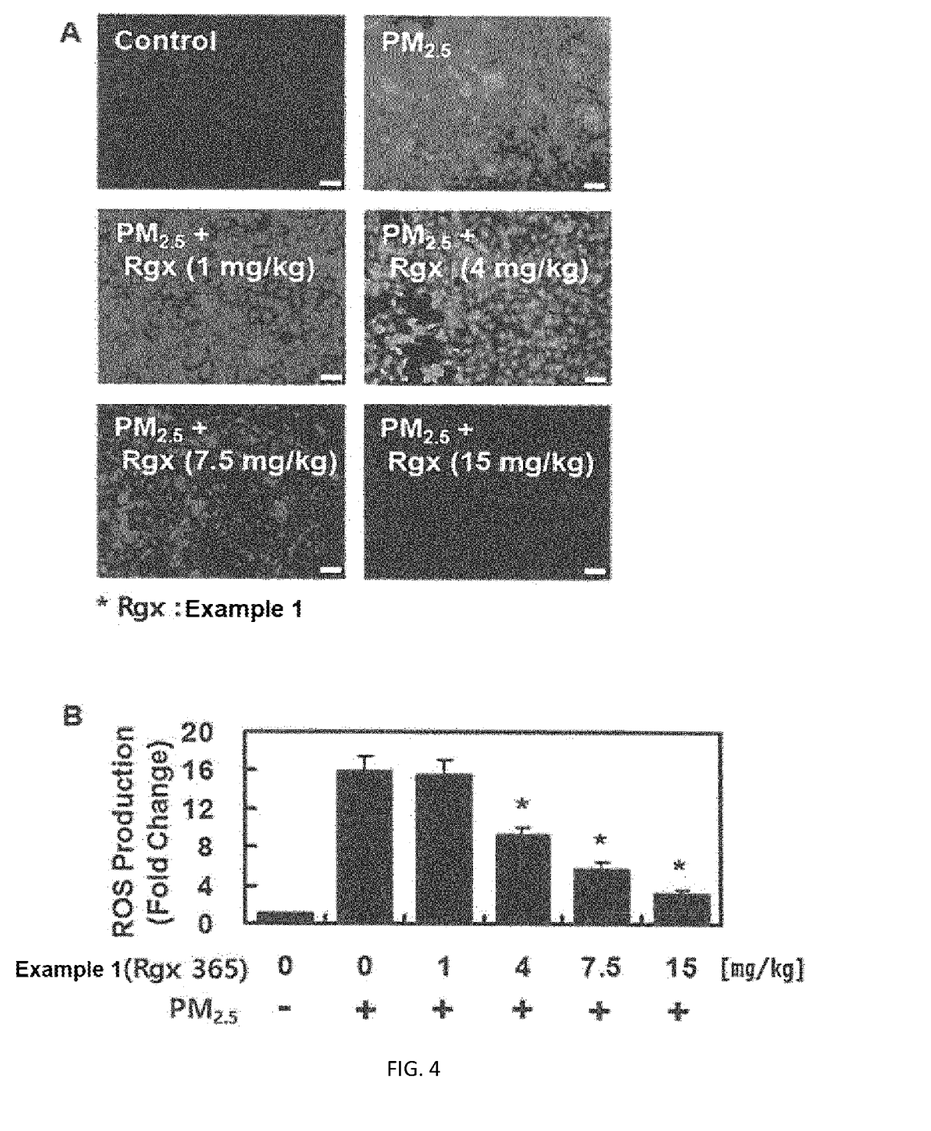
FIGS. 4A and 4B are fluorescent images and a graph showing changes of reactive oxygen species (ROS) production in fine dust-treated mouse lung microvascular endothelial cells with treatment concentrations of the mixture (RGX-365) of Example 1 of the present disclosure.

As can be seen in FIGS. 4A and 4B, the ROS production increased by fine dust was reduced by the mixture (RGX 365) of Example 1 of the present disclosure in a dose-dependent manner. Thus, the data demonstrate that the mixture containing Rg2, Rg4, Rg6, and Rh1 in Example 1 of the present disclosure can be used as a composition highly inhibitory of fine dust-induced generation of reactive oxygen species (ROS).

Experimental Example 5

Inhibitory Effect on Fine Dust-Induced Inflammation in Animal Model

Experimental Example 5-1

Permeability Assay

First, 7-week-old male Balb/c mice (weighing 27 g, Orient Bio Co., Sungnam, Republic of Korea) were acclimated at a temperature of 20-25° C. and a relative humidity of 40-45% for 12 days on ah 12-hr light/12-hr dark cycle. The mice used in experiments were treated according to the guideline for the Care and use of Laboratory Animals at Kyungpook National University (IRB No. KNU 2017-101).

Oral administration was made of the ginsenoside mixture (RGX-365) of Example 1 at a dose of 0, 1, 2, 4, 7.5, or 15 mg/kg, or each of the reference standard ginsenosides Re, Rg4, Rg6, and Rh1 or the ginsenoside mixture of Comparative Example 1 at a dose of 15 mg/kg for 10 days to the mice to which fine dust ($PM_{2.5}$, 1 mg/kg in 100 µl of saline, 10 days) was then administered intratracheally as previously reported [Wang, H. et al., Sci Rep., 7, 44256, 2017]. After 10 days of the intratracheal instillation of fine dust, the male mice anesthetized with 2% isoflurane (Forane, JW Pharmaceutical, South Korea) were each sacrificed and injected intravenously with a 1% Evans blue solution in physiological saline as previously described [Bae, J. S. et al., Blood, 118(14), 3952-3959, 2011; Jung, B. et al., BMB Rep., 49(4), 214-219, 2016]. Permeability was measured using an ELISA plate reader and the results are depicted in FIGS. 5A and 5B.

Figure 5:
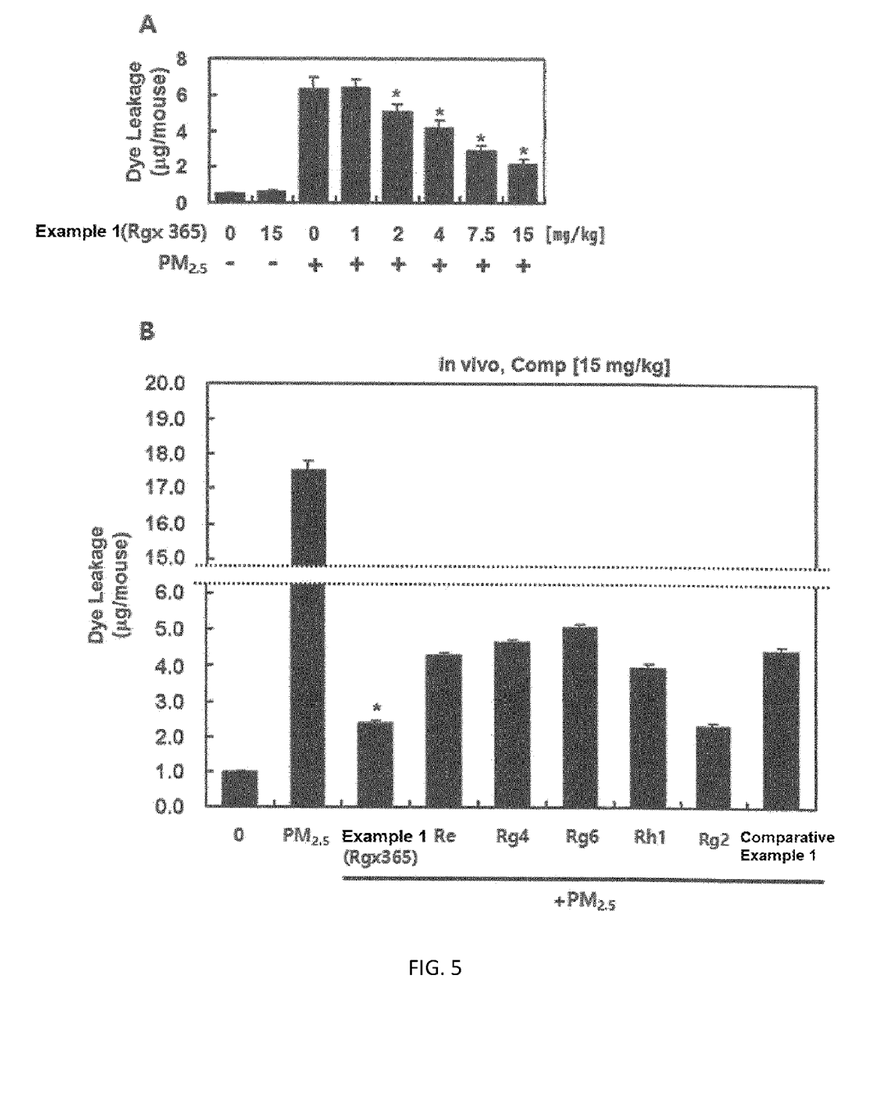
FIG. 5A is a graph showing dye leakage from fine dust-treated mice according to treatment concentrations of the mixture (RGX-365) of Example 1 of the present disclosure and FIG. 5B is a graph showing dye leakage from fine dust-treated mice according to treatment with the mixture (RGX-365) of Example 1 of the present disclosure, individual ginsenosides Re, Rg4, Rg6, Rh1, and Rg2, and the mixture of Comparative Example 1.

With reference to FIGS. 5A and 5B, dye leakage that was greatly induced by fine dust was reduced by treatment with the mixture (Rgx 365) of Example 1 in a dose-dependent manner. Compared with individual ginsenosides Re, Rg4, Rg6, and Rh1, the mixture of Example 1 of the present disclosure remarkably inhibited dye leakage particularly by protecting vessel walls against injury.

From the results, it is understood that the mixture containing ginsenosides Rg2, Rg4, Rg6, and Rh1 at specific contents according to the present disclosure is more effective for inhibiting fine dust-induced inflammation than individual ginsenosides Re, Rg4, Rg6, and Rh1.

Experimental Example 5-2

Counts of Leukocyte and Expression of Inflammation-Related Factor

Figure 6:
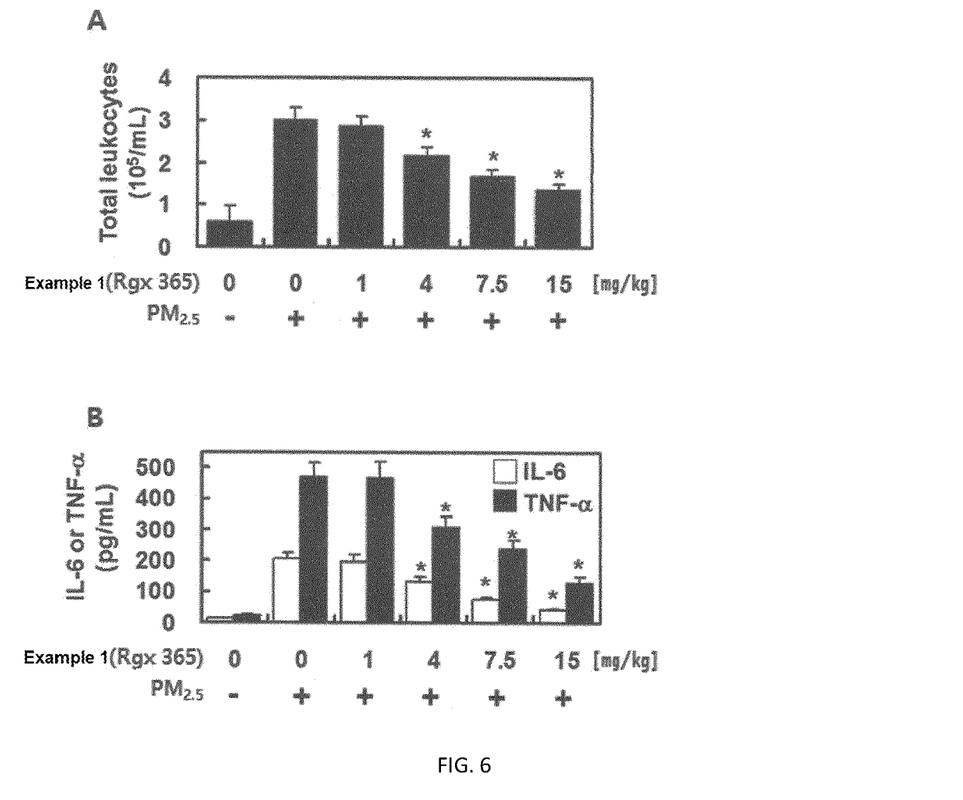
FIG. 6A is a graph showing counts of leukocytes in fine dust-treated mouse bronchoalveolar lavage fluid according to treatment concentrations of the mixture (RGX-365) of Example 1 of the present disclosure and FIG. 6B is a graph showing production changes of IL-6 and TNF-α in fine dust-treated mouse bronchoalveolar lavage fluid according to treatment concentrations of the mixture (RGX-365) of Example 1 of the present disclosure.

Oral administration was made of the ginsenoside mixture (RGX-365) of Example 1 at a dose of 0, 1, 2, 4, 7.5, or 15 mg/kg, or each of the reference standard ginsenosides Re, Rg4, Rg6, Rh1, and Rg2, or the ginsenoside mixture of Comparative Example 1 at a dose of 15 mg/kg for 10 days to the mice to which fine dust was intratracheally instilled for 10 days, as in Experimental Example 5-1. The mice were sacrificed before bronchoalveolar lavage fluid (BAL) was obtained therefrom. The BAL was washed with 5 ml of physiological saline and mixed with 0.38 ml of Turk's solution (0.01% crystal violet in 3% acetic acid). Leukocytes were counted under an optical microscope and are depicted in FIG. 6A. Concentrations of the inflammation-related factors IL-6 and TNF-α in the bronchoalveolar lavage fluid were measured using ELISA kits (R&D Systems, Minneapolis, MN) and are depicted in FIG. 6B.

With reference to FIGS. 6A and 6B, the ginsenoside mixture (RGX-365) of Example 1 of the present disclosure is observed to reduce the number, increased by fine dust, of leukocytes in bronchoalveolar lavage fluid in a dose-dependent manner and inhibit the fine dust-induced increase of the inflammation-related cytokines IL-6 and TNF-α in bronchoalveolar lavage fluid.

Experimental Example 5-3

H&E Staining

Examination was made of histological changes in fine dust-treated mouse lung tissues and effects of the ginsenoside mixture (RGX-365) of the present disclosure thereon. In this regard, oral administration was made of the ginsenoside mixture (RGX-365) of Example 1 at a dose of 0 or 15 mg/kg for 10 days to the mice to which fine dust was intratracheally instilled for 10 days, as in Experimental Example 5-1. Then, the mice were sacrificed before lung tissues were obtained therefrom. The tissues were fixed with 4% formaldehyde solution in PBS at 4° C. for 20 hours, dehydrated with ethanol, and embedded in paraffin. Subsequently, the paraffin-embedded tissue was sectioned into 4-μm-thick slices which were mounted on slides and subjected to deparaffinization at 60° C. in an oven, rehydration, and staining with hematoxylin. The slides were quickly dipped three times in 0.3% acidic alcohol to remove an excess of the dye and then counterstained with eosin. An excess of the dye was removed by washing with ethanol and xylene and the sample were put under cover slip. Optical microscopy analysis of the lung specimen was carried out as previously reported [Ozdulger, A. et al., Shock, 19(4), 366-372, 2003], and histological changes of the lung tissue are depicted in FIG. 7.

Figure 7:
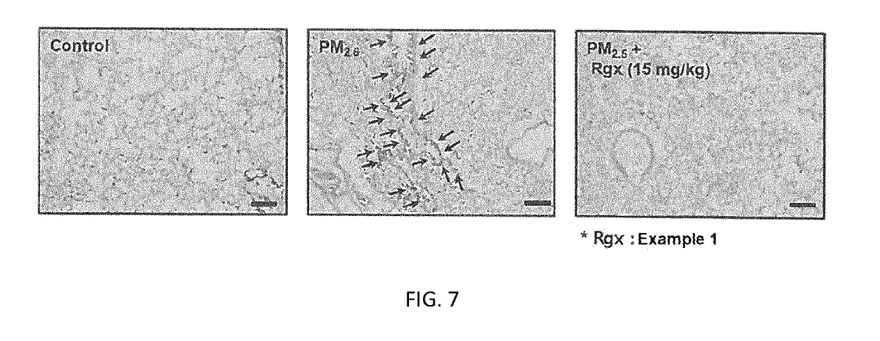
FIG. 7 shows leukocytic infiltration into fine dust-treated mouse lung tissues according to treatment with the mixture (RGX-365) of Example 1 of the present disclosure.

Referring to FIG. 7, leukocytic infiltration was observed to increase in the fine dust-instilled lung tissue ($PM_{2.5}$), compared to the lung tissue having no find dust instilled thereto (Control). Treatment with the mixture (RGX-365) of Example 1 according to the present disclosure remarkably reduced fine dust-induced leukocytic infiltration into mouse lung tissues.

Taken together, the data demonstrate that the ginsenoside Rg2-enriched mixture of ginsenosides Rg2, Rg4, Rg6, and Rh1, prepared in Example 1 of the present disclosure, is superb in the prevention or treatment of fine dust-induced respiratory diseases and as such, can find advantageous applications as a composition for prevention or treatment of fine dust-induced respiratory diseases.

FORMULATION EXAMPLE 1

Preparation of Tablet

With 20 g of the mixture (Rgx 365) of Example 1 according to the present disclosure were combined 175.9 g of lactose, 180 g of potato starch, and 32 g of colloidal silicate. The combination was added with a 10% gelatin solution, ground, and let to pass through a 14-mesh sieve. The resulting mixture was dried, and prepared, together with 160 g of potato starch, 50 g of talc, and 5 g of magnesium stearate, into a tablet.

FORMULATION EXAMPLE 2

Preparation of Capsule>

With 100 mg of the mixture (Rgx 365) of Example 1 according to the present disclosure were combined 100 mg of maize starch, 100 mg of lactose, and 2 mg of magnesium stearate. The ingredients were blended and loaded into a gelatin capsule to afford a capsule according to a typical capsule preparation method.

FORMULATION EXAMPLE 3

Preparation of Injection

Together with 0.6 g of sodium chloride and 0.1 g of ascorbic acid, 1 g of the mixture (Rgx 365) of Example 1 according to the present disclosure was dissolved in distilled water to form a final volume of 100 ml which was then charged into a bottle and heated at 20° C. for 30 min for sterilization.

FORMULATION EXAMPLE 4

Preparation of Health Functional Food

A combination of 20 g of the mixture (Rgx 365) of Example 1 according to the present disclosure, a suitable amount of vitamins including 70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of nicotinamide, 50 μg of folic acid, 0.5 mg of calcium pantothenate, and a suitable amount of minerals including 1.75 mg of ferrous sulfate, 0.82 mg of zinc oxide, 25.3 mg of magnesium carbonate, 15 mg of potassium phosphate monobasic, 55 mg of potassium phosphate dibasic, 90 mg of potassium citrate, 100 mg of calcium carbonate, and 24.8 mg of magnesium chloride were blended and prepared into granules according to uses. However, the combination may be prepared into various modified formulations. In addition, any modification may be made to the composition ratio between the vitamin and the mineral mixtures. The ingredients may be mixed and prepared into food formulations according to ordinary health food preparation method.

FORMULATION EXAMPLE 5

Preparation of Health Functional Beverage

A beverage was prepared by stirring, heating, filtering, sterilizing, and refrigerating a combination of 1 g of the mixture (Rgx 365) of Example 1 according to the present disclosure, 0.1 g of citric acid, 100 g of fructooligosaccharide, and 900 g of purified water according to an ordinary beverage preparation method.

The invention claimed is:
1. A method for treating a fine dust-induced respiratory disease comprising administering to a subject in need thereof a therapeutically effective amount of a composition comprising a mixture containing ginsenosides Rg2, Rg4,

Rg6, and Rh1, wherein the mixture contains 35-45% by weight of ginsenoside Rg2, 30-40% by weight of ginsenoside Rg4, 10-20% by weight of ginsenoside Rg6, and 1-5% by weight of ginsenoside Rh1.

2. The method of claim 1, wherein the fine dust-induced respiratory disease is selected from the group consisting of inflammatory lung disease, asthma, chronic obstructive pulmonary disease, allergic rhinitis, cough, bronchitis, laryngopharyngitis, tympanitis, tonsillitis, sinusitis, pneumonia, pulmonary fibrosis, and laryngitis.

* * * * *

UNITED STATES PATENT AND TRADEMARK OFFICE
CERTIFICATE OF CORRECTION

| | | |
|---|---|---|
| PATENT NO. | : 12,370,205 B2 | Page 1 of 1 |
| APPLICATION NO. | : 17/602684 | |
| DATED | : July 29, 2025 | |
| INVENTOR(S) | : Gyu Yong Song et al. | |

It is certified that error appears in the above-identified patent and that said Letters Patent is hereby corrected as shown below:

On the Title Page

After (65) Prior Publication Data US 2022/0160738 A1 May 26, 2022 insert the following:
-- (30) Foreign Application Priority Data
April 9, 2019 (KR) .........10-2019-0041447
April 9, 2019 (KR) .........10-2019-0041458 --

Signed and Sealed this
Thirtieth Day of September, 2025

John A. Squires
*Director of the United States Patent and Trademark Office*